United States Patent
Komatsubara et al.

(10) Patent No.: US 9,943,451 B2
(45) Date of Patent: Apr. 17, 2018

(54) ABSORBENT ARTICLE FOR PET

(75) Inventors: Daisuke Komatsubara, Kagawa (JP); Takeshi Ikegami, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 496 days.

(21) Appl. No.: 14/123,207

(22) PCT Filed: Jun. 1, 2012

(86) PCT No.: PCT/JP2012/003640
§ 371 (c)(1),
(2), (4) Date: Nov. 30, 2013

(87) PCT Pub. No.: WO2012/164962
PCT Pub. Date: Dec. 6, 2012

(65) Prior Publication Data
US 2014/0107606 A1    Apr. 17, 2014

(30) Foreign Application Priority Data

Jun. 2, 2011   (JP) ................................. 2011-124672

(51) Int. Cl.
*A61F 13/15*    (2006.01)
*A61F 13/20*    (2006.01)
(Continued)

(52) U.S. Cl.
CPC .......... *A61F 13/5633* (2013.01); *A01K 23/00* (2013.01); *A61D 99/00* (2013.01)

(58) Field of Classification Search
CPC .. Y10T 428/24008; A61F 13/62; A61F 13/56; A61F 13/5605; A61F 2013/5683;
(Continued)

(56) References Cited

U.S. PATENT DOCUMENTS 4,834,743 A * 5/1989 Valerio ................... A61M 1/02
                                                         604/403
4,996,949 A * 3/1991 Wunderman .......... A01K 23/00
                                                         119/850
(Continued)

FOREIGN PATENT DOCUMENTS

JP    2004-159592 A    6/2004
JP    2007-020533 A    2/2007
(Continued)

OTHER PUBLICATIONS

"Configure." Merriam-Webster.com. Merriam-Webster, n.d. Web. Nov. 27, 2016.*
(Continued)

*Primary Examiner* — Michele M Kidwell
(74) *Attorney, Agent, or Firm* — Hauptman Ham, LLP

(57) ABSTRACT

An absorbent article for pet includes: a top sheet; a back surface layer; an absorbent core; a first end portion and a second end portion opposing to each other in a longitudinal direction; a first side portion and a second side portion opposing to each other in a width direction; an engaging member disposed in the vicinity of the first end portion along the width direction of the absorbent article; a first engaged portion engageable with the engaging member and is disposed in the vicinity of the second end portion, at least at a position faceable a central portion of the engaging member and a second engaged portion engageable with the engaging member with an engagement force smaller than an engagement force of the first engaged portion with the engaging member, and is disposed at least at a position faceable one of opposite ends of the engaging member.

18 Claims, 15 Drawing Sheets

(51) Int. Cl.
  *A61F 13/56*  (2006.01)
  *A01K 23/00*  (2006.01)
  *A61D 99/00*  (2006.01)
(58) Field of Classification Search
  CPC .......... A61F 13/581; A61F 2013/15186; A41F 1/00; A61D 9/00; A61D 99/00
  See application file for complete search history.

(56) References Cited

U.S. PATENT DOCUMENTS

| | | | | |
|---|---|---|---|---|
| 5,137,508 | A | * | 8/1992 | Engman .................. A61D 9/00 119/850 |
| 9,113,612 | B2 | * | 8/2015 | Komatsubara ......... A01K 23/00 |
| 9,265,234 | B2 | * | 2/2016 | Komatsubara ......... A01K 23/00 |
| 2002/0022819 | A1 | * | 2/2002 | Ronnberg ............... A61F 13/64 604/386 |
| 2005/0154367 | A1 | * | 7/2005 | Ikegami ................. A01K 23/00 604/389 |
| 2007/0129702 | A1 | | 6/2007 | Gribben |
| 2009/0069776 | A1 | * | 3/2009 | Utsunomiya ......... A61F 13/627 604/385.03 |
| 2011/0209675 | A1 | * | 9/2011 | Esperon ................. A01K 23/00 119/868 |
| 2014/0083372 | A1 | * | 3/2014 | Komatsubara ......... A01K 23/00 119/850 |
| 2014/0090608 | A1 | * | 4/2014 | Komatsubara ......... A01K 23/00 119/869 |
| 2014/0290589 | A1 | * | 10/2014 | Komatsubara ......... A01K 23/00 119/869 |

FOREIGN PATENT DOCUMENTS

| | | |
|---|---|---|
| JP | 2008-006272 A | 1/2008 |
| JP | 3141580 U | 5/2008 |
| JP | 2009-254278 A | 11/2009 |

OTHER PUBLICATIONS

International Search Report for PCT/JP2012/003640 dated Aug. 7, 2012.

* cited by examiner

ABSORBENT ARTICLE FOR PET

RELATED APPLICATIONS

The present application is a National Phase entry of International Application Number PCT/JP2012/003640, filed Jun. 1, 2012, which claims priority to Japanese Application Number 2011-124672 filed Jun. 2, 2011.

TECHNICAL FIELD

The present disclosure relates to an absorbent article for pet.

BACKGROUND ART

A disposable diaper for pet to be used for a pet, such as a dog or cat, is known to the inventors. Such a disposable diaper for pet catches feces and urine of the pet by covering the anus and the urethral opening positioned between bases of hind legs when being worn.

Some pets (for example miniature dachshund having short legs and a long abdomen) have the urethral opening located further toward the front than a position between bases of hind legs. In addition, male dogs have the urethral opening located further toward the front compared to female dogs. If the disposable diaper for pet is used for pets having the urethral opening further toward the front than a position between bases of hind legs, the urethral opening may not be covered by the diaper and urine may leak.

Given this, an absorbent article for pet that is configured in a belt-like shape and to be worn in a state of being wrapped around the pet's waist is also known to the inventors.

Such an absorbent article for pet configured in a belt-like shape can cover the urethral opening, regardless of position thereof.

The absorbent article for pet is put on the pet in the following steps, for example.

First, the first end portion of the absorbent article for pet is placed on the back of the pet and the first end portion is held by one hand of a user, thereby keeping the first end portion in close contact with the back of the pet. Next, in a state in which the first end portion is held by one hand, the second end portion located on a second end side of the absorbent article for pet is held by the other hand and wrapped around the pet's body to cover an abdomen of the pet. And then, the second end portion of the absorbent article for pet is pulled to bring a side portion of the absorbent article for pet in a longitudinal direction into close contact with the waist of the pet, and, in this state, the inner surface of the second end portion of the absorbent article for pet and the outer surface of the first end portion is engaged with each other with some engagement members. The absorbent article for pet can thus be maintained in a state of being appropriately wrapped around the pet's waist.

Here, the first end portion and the second end portion of the absorbent article for pet are joined by engaging a hook member provided on an outer face of the first end portion with a loop member provided on an inner face of the second end portion, or by arranging an adhesive tape on the outer face of the first end portion and attaching the inner face of the second end portion to the adhesive tape.

However, the inventor(s) has recognized that if an engagement force of the nonwoven fabric constituting the second end portion with which the hook member or the adhesive tape is engaged is too high, it would be difficult to remove the hook member or the adhesive tape from the nonwoven fabric of the second end portion. As a result, the nonwoven fabric of the second end portion may be damaged upon removal, leading to a problem of exposure of an absorbent core and the like. On the other hand, if the engagement force of the nonwoven fabric is too low, the first end portion may be detached from the second end portion due to movement of the pet wearing the absorbent article for pet.

SUMMARY OF INVENTION

According to some embodiments of the present invention, an absorbent article for pet is configured to be worn in a state of being wrapped around a waist of a pet. The absorbent article for pet includes: a liquid permeable top sheet; a liquid impermeable back surface layer; an absorbent core disposed between the top sheet and the back surface layer; a first end portion and a second end portion opposing to each other in a longitudinal direction of the absorbent article for pet; a first side portion and a second side portion opposing to each other in a width direction of the the absorbent article for pet; an engaging member that is disposed in the vicinity of the first end portion along a width direction of the absorbent article for pet; a first engaged portion that is engageable with the engaging member and is disposed in the vicinity of the second end portion, at least at a position facing a central portion of the engaging member in a longitudinal direction thereof in a state in which the absorbent article for pet is wrapped around the waist of the pet; and a second engaged portion that is engageable with the engaging member with an engagement force smaller than an engagement force of the first engaged portion with the engaging member, and is disposed at least at a position facing one of opposite ends of the engaging member in the longitudinal direction thereof in the state in which the absorbent article for pet is wrapped around the waist of the pet.

DESCRIPTION OF EMBODIMENTS

Embodiments of the absorbent article for pet will be described hereinafter with reference to the drawings.

First, the absorbent article for pet according to the first embodiment will be described hereinafter with reference to FIGS. 1 to 7.

Figure 1:
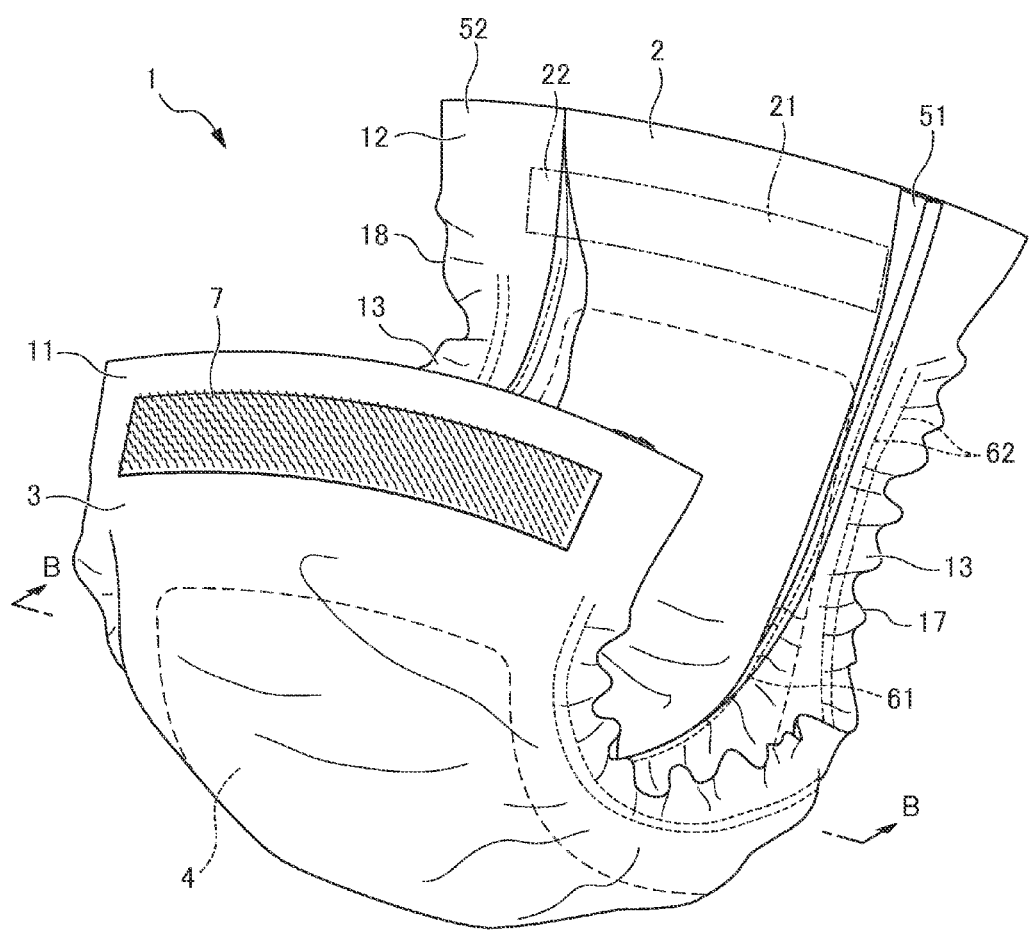
FIG. 1 is a perspective view showing an absorbent article for pet according to a first embodiment of the present invention.
Figure 2:
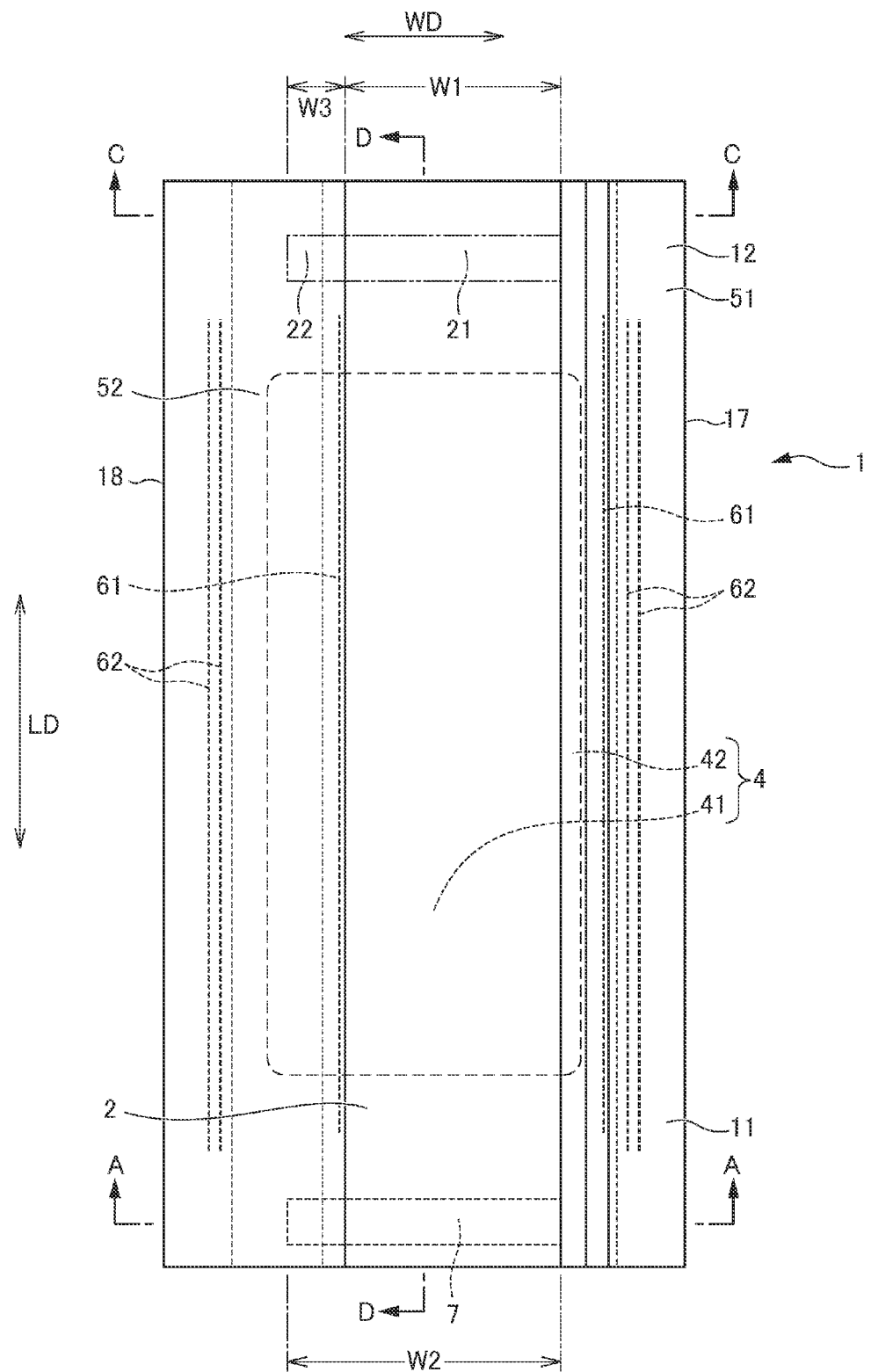
FIG. 2 is a plan view of the absorbent article for pet according to the first embodiment, as viewed from a top sheet side.

As shown in FIGS. 1 and 2, an absorbent article for pet 1 according to the first embodiment is configured in a rectangular shape with a first end portion 11 and a second end portion 12 opposing to each other and a back side portion 17 as the first side portion and a front side portion 18 as the second side portion opposing to each other and orthogonal to the first end portion 11 and the second end portion 12. The absorbent article for pet 1 is to be worn in a state of being wrapped around the pet's waist. The absorbent article for pet 1 is especially preferably used for pet having a urethral opening further toward the front than a position between bases of hind legs (for example, a dog having short legs and long abdomen, such as miniature dachshund).

The absorbent article for pet 1 includes, as shown in FIGS. 1 to 7: a liquid permeable top sheet 2; a back surface sheet 31 and a waterproof sheet 32 constituting the liquid impermeable back surface layer (back sheet) 3; an absorbent core 4; a pair of side sheets 51, 52 including a first side sheet 51 and a second side sheet 52; a first elastic member 61; a second elastic member 62; a hook tape 7 as the engaging member.

The top sheet 2 is configured in a rectangular shape. The top sheet 2 mainly constitutes a surface of a side to be in contact with the pet's body. As the top sheet 2, a perforated or non-perforated nonwoven fabric or a porous plastic sheet can be used. In the first embodiment, the top sheet 2 is preferably configured with a nonwoven fabric to be engageable with the hook tape 7 (described later). As a top sheet 2, air-through nonwoven fabric is used. The density of the nonwoven fabric that forms the top sheet 2 is 0.01 g/cm³ to 1.0 g/cm³.

Figure 4:
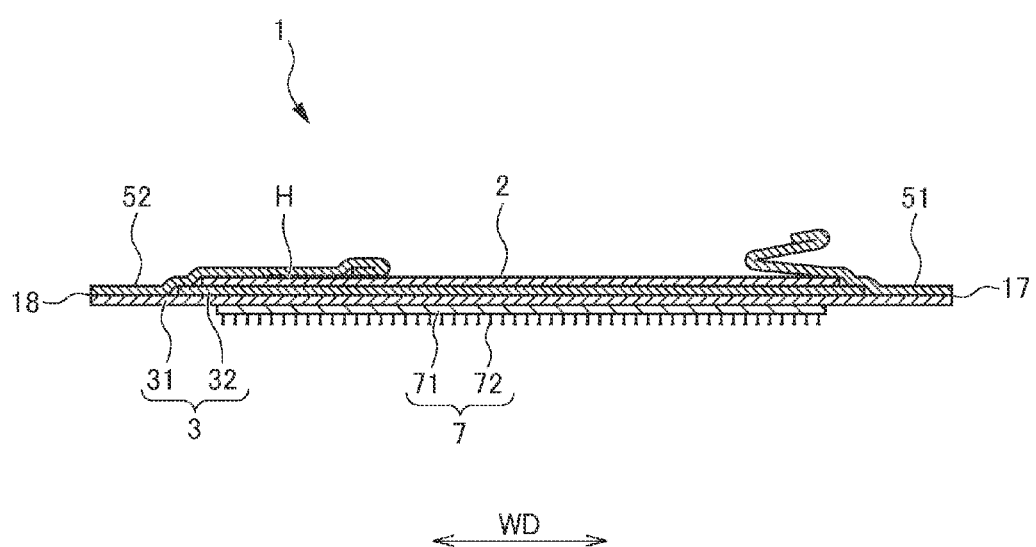
FIG. 4 is a cross-sectional view taken along the line A-A of FIG. 2.
Figure 5:
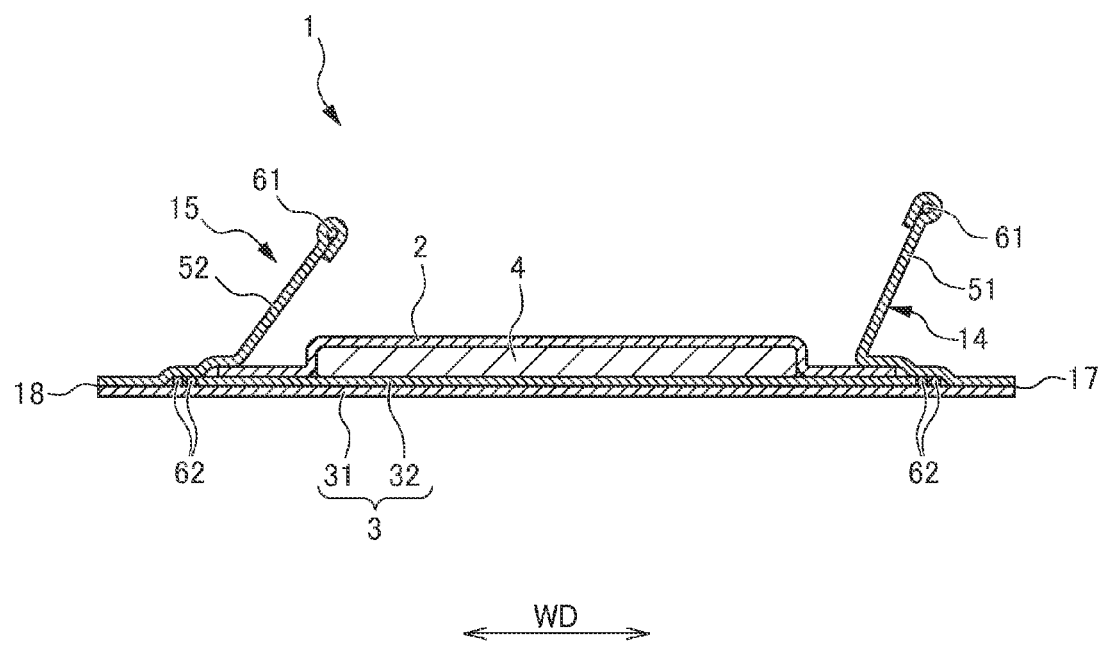
FIG. 5 is a cross-sectional view taken along the line B-B of FIG. 1.
Figure 6:
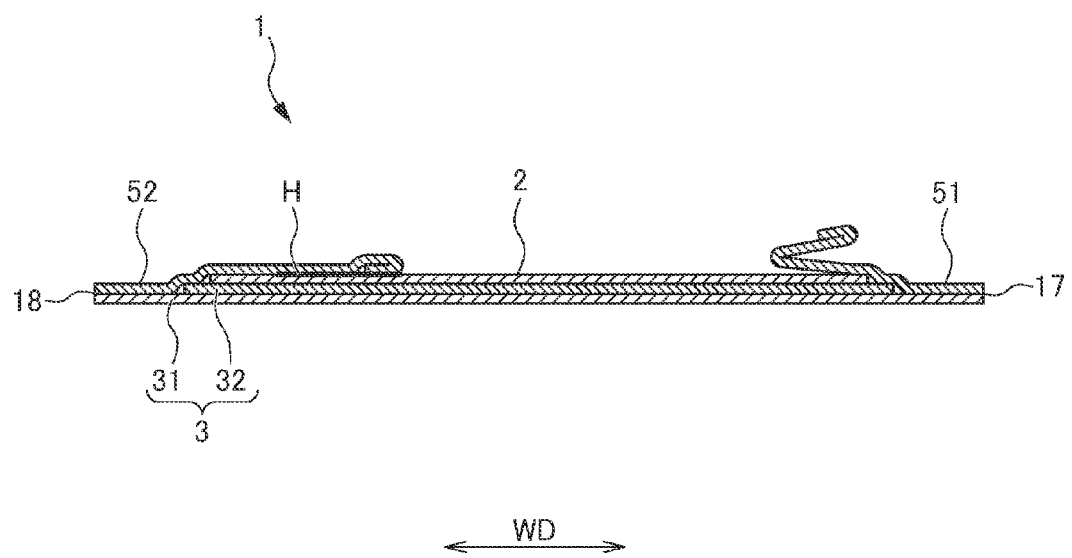
FIG. 6 is a cross-sectional view taken along the line C-C of FIG. 2.

The back surface sheet 31 is configured in a rectangular shape that is wider than, and has substantially the same length as, the top sheet 2, as shown in FIGS. 4 to 6. The back surface sheet 31 constitutes a surface of the absorbent article for pet 1, on a side not to be in contact with the pet's body.

The waterproof sheet 32 is configured to be smaller in width than the back surface sheet 31 and disposed on a top sheet side of the back surface sheet 31.

As the back surface sheet 31 and the waterproof sheet 32, a hydrophobic nonwoven fabric, a liquid impermeable plastic film, a laminated sheet made of the nonwoven fabric and the liquid impermeable plastic film, spun bond nonwoven fabric, an SMS nonwoven fabric made by sandwiching a high-water resistance melt-blown nonwoven fabric with a high-strength spun-bond nonwoven fabric, and the like can be used. The density of the nonwoven fabrics that form the back surface sheet 31 and the waterproof sheet 32 are in the range of 0.001 g/cm³ to 0.3 g/cm³.

Figure 3:
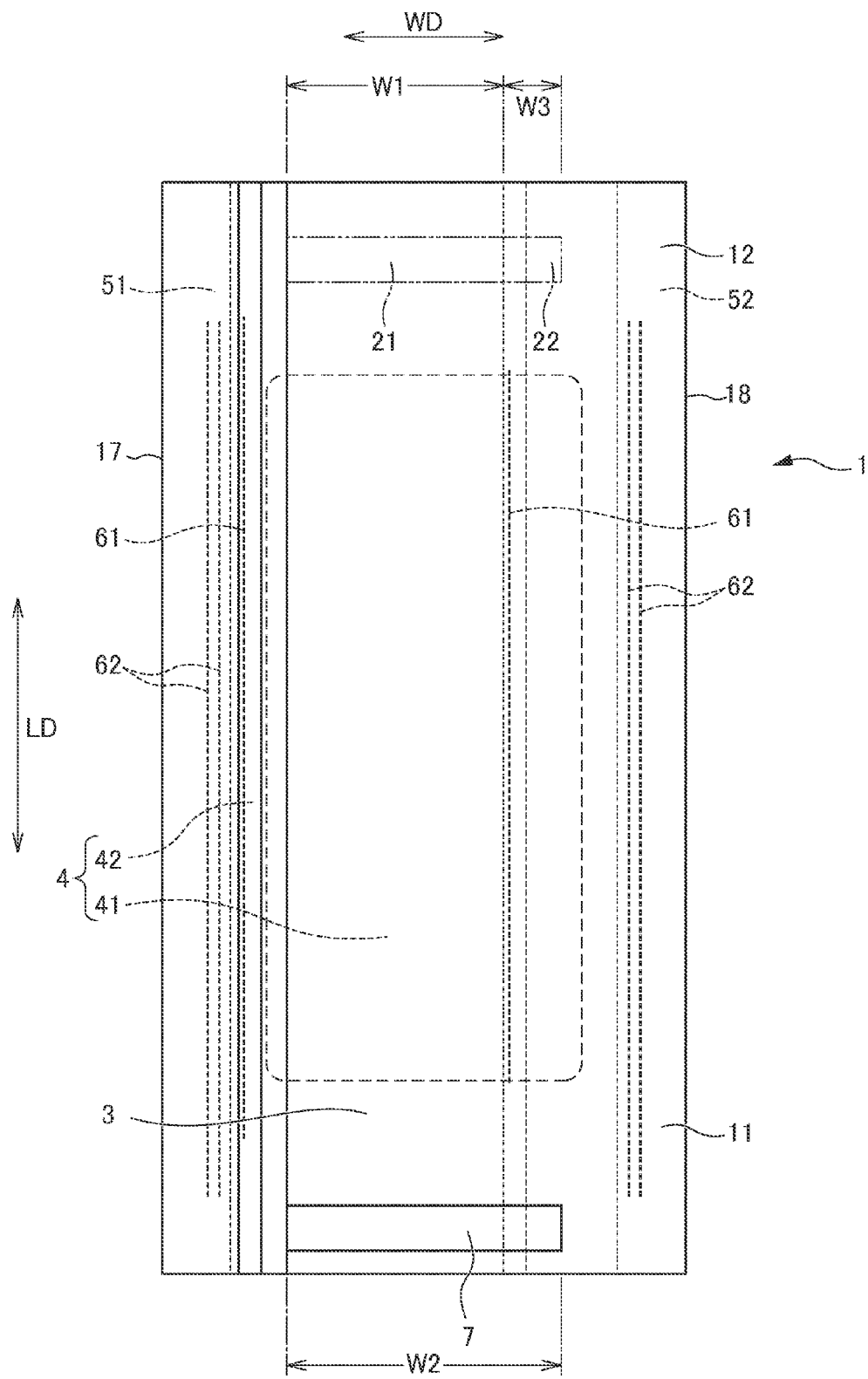
FIG. 3 is a plan view of the absorbent article for pet according to the first embodiment, as viewed from a back surface layer side.
Figure 7:
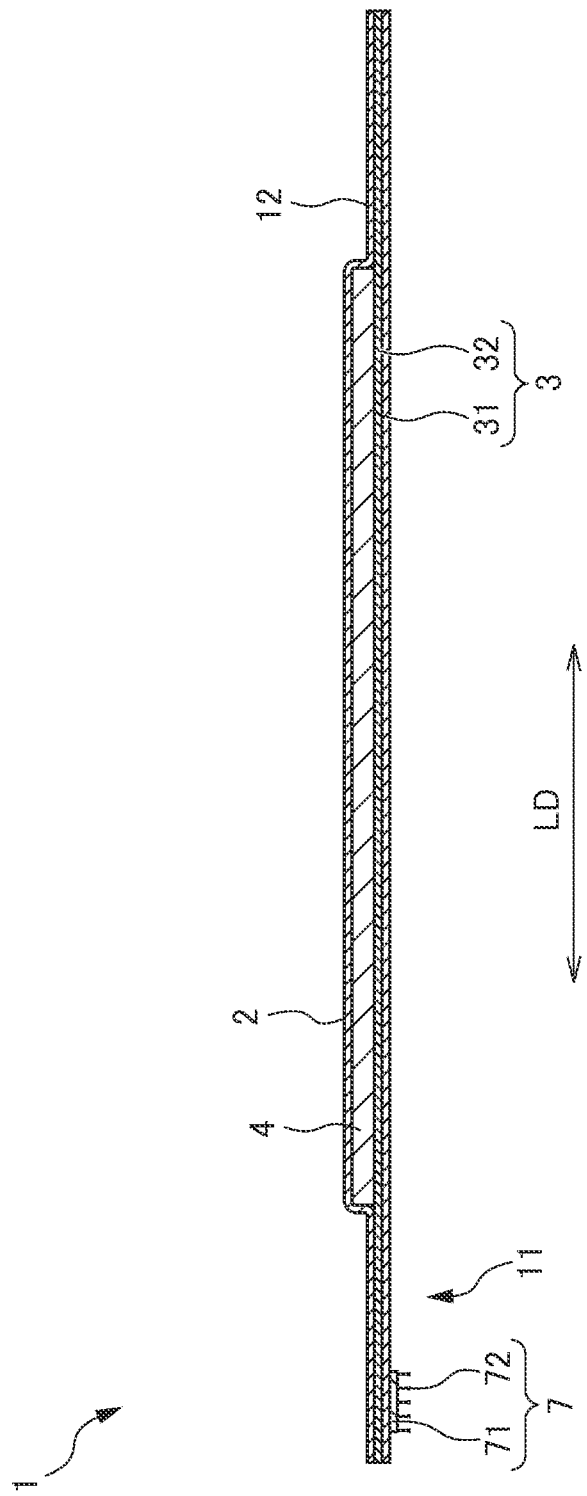
FIG. 7 is a cross-sectional view taken along the line D-D of FIG. 2.

The absorbent core 4 is disposed between the top sheet 2 and the back surface layer 3 that are layered, as shown in FIGS. 5 and 7. The absorbent core 4 is configured in a rectangular shape smaller in width and length than the top sheet 2 and the back surface sheet 31. As shown in FIGS. 2 and 3, in planar view, the absorbent core 4 is disposed in a substantially central portion in the width direction of the top sheet 2 and the back surface sheet 31, and extends from one end side to another end side in the longitudinal direction. As the absorbent core 4, fluff pulp and high absorbance polymer wrapped with a core wrapping material, such as tissue can be used.

As the fluff pulp used in the absorbent core 4, chemical pulp, cellulose fiber, and artificial cellulose fiber, such as rayon, acetate, and the like can be exemplified. As the high absorbance polymer, granulous or fibrous polymer of starch, acrylic acid, and amino acid can be exemplified.

The pair of side sheets 51, 52 are, as shown in FIG. 2, configured in an elongated rectangular shape along the longitudinal direction LD of the absorbent article for pet 1 and disposed respectively on the back side portion 17 and the front side portion 18 on the top sheet 2. The pair of side sheets 51, 52 are configured to have substantially the same length as the top sheet 2 and the back surface sheet 31. As shown in FIGS. 4 to 6, outer edges of the pair of side sheets 51, 52 correspond to side edges of the back surface sheet 31. The outer edges of the pair of side sheets 51, 52 are joined with the side edges of the back surface sheet 31.

At least a part of the inner edges of the pair of side sheets 51, 52 is a free-end, as shown in FIGS. 1 and 5. More specifically, the pair of side sheets 51, 52 includes the first side sheet 51 disposed in the back side portion 17 and the second side sheet 52 disposed in the front side portion 18. Here, the back side portion 17 is disposed on a back side of the pet's body during use of the absorbent article for pet 1; and the front side portion 18 is disposed on a front side of the pet's body during use of the absorbent article for pet 1.

As shown in FIGS. 4 to 6, the inner edge of the first side sheet 51 is not joined with the top sheet 2 in an overall length in the longitudinal direction LD of the absorbent article for pet 1. In other words, the inner edge of the first side sheet 51 is a free end in an overall length in the longitudinal direction LD of the absorbent article for pet 1. In addition, the inner edge of the first side sheet 51 is folded outward in the width direction WD of the absorbent article for pet 1, in the first end portion 11 and the second end portion 12, as shown in FIGS. 4 and 6.

The inner edge of the second side sheet 52 is joined to the top sheet 2 in the first end portion 11 and the second end portion 12, by hotmelt adhesive H as shown in FIGS. 4 and 6. In addition, as shown in FIG. 5, the inner edge of the second side sheet 52 is a free end, except for the first end portion and the second end portion in the longitudinal direction LD of the second side sheet 52 which are joined to the top sheet 2 in the first end portion 11 and the second end portion 12, respectively.

As the first side sheet 51 and the second side sheet 52, a water repellent or hydrophobic sheet is preferably used. More specifically, various nonwoven fabrics, such as spun lace nonwoven fabric, spun bond nonwoven fabric, thermal bond nonwoven fabric, melt-blown nonwoven fabric, SMS nonwoven fabric, needle-punched nonwoven fabric, air-through nonwoven fabric and the like can be used. As the fiber constituting the nonwoven fabric, synthetic fiber of olefin, polyester, polyamide and the like such as polyethylene and polypropylene; regenerated fiber, such as rayon and cupra; and natural fiber, such as cotton can be used. In this embodiment, as the first side sheet 51 and the second side sheet 52, SMS nonwoven fabric is used. The density of the nonwoven fabrics that form the first side sheet 51 and the second side sheet 52 are 0.001 g/cm$^3$ to 0.3 g/cm$^3$.

The first elastic member 61 is disposed in the vicinity of the inner edge of the first side sheet 51 and the second side sheet 52, as shown in FIGS. 1 to 3. More specifically, the first elastic member 61 is sandwiched by the side sheet that is folded back to the inner edge side and fixed to the side sheet by a hotmelt adhesive (not illustrated) in an extended state as shown in FIG. 5. The first elastic member 61 is, in the extended state, greater in length than the absorbent core 4 in the longitudinal direction LD and is disposed in the first side sheet 51 and the second side sheets 52 as shown in FIG. 2.

The second elastic member 62 is disposed in the front side portion 18 and the back side portion 17, as shown in FIGS. 1 to 3. More specifically, the second elastic member 62 is disposed between the first side sheet 51 and the back surface sheet 31, and between the second side sheet 52 and the back surface sheet 31, as shown in FIG. 5. In addition, the second elastic member 62 is fixed to the side sheets 51, 52 and the back surface sheet 31 by a hotmelt adhesive.

The second elastic member 62 is, in the extended state, greater in length than the absorbent core 4 in the longitudinal direction LD and is disposed in the front side portion 18 and the back side portion 17.

As the first elastic member 61 and the second elastic member 62, any material that is elongated and stretchable can be used, for example: natural rubber, such as filiform rubber and flat rubber; thermoplastic elastomer, such as urethane, ethylene-vinyl acetate copolymer (EVA), and PE. More specifically, as the thermoplastic elastomer, polybutadiene, polyisoprene, styrene-butadiene copolymer, styrene-isoprene copolymer, polyurethane, ethylene-vinyl acetate copolymer, ethylene-alpha-olefin copolymer and the like that are processed to be filiform or formed in a film and then slitted into thin strips can be exemplified.

The hook tape 7 is disposed in the vicinity of the first end portion 11 of the absorbent article for pet 1, as shown in FIGS. 1 to 3. In the first embodiment, the hook tape 7 is disposed on an outer face of the first end portion 11, in other words on the back surface sheet 31 side of the first end portion 11. The hook tape 7 is configured in a rectangular shape and disposed such that the longitudinal direction thereof is along the width direction WD of the absorbent article for pet 1. In addition, the hook tape 7 is attached to a position spaced apart from the side edge of the first end portion 11 by a predetermined distance.

The hook tape 7 is configured in a length allowing engagement with the top sheet 2 and the second side sheet 52 in the vicinity of the second end portion 12 in a state in which the absorbent article for pet 1 is wrapped around the pet's waist.

As shown in FIG. 4, the hook tape 7 includes a belt-shaped base portion 71 and a plurality of hook portions 72 provided on one face of the base portion 71. The hook tape 7 is attached to the back surface sheet 31 such that the face on which the plurality of hook portions 72 is formed is directed outward.

The first engaged portion 21 and the second engaged portion 22 are, as shown in FIGS. 1 to 3, positioned on the top sheet side in the vicinity of the second end portion 12, and constitute a region that is engageable with the hook tape 7 in a state in which the absorbent article for pet 1 is wrapped around the pet's waist.

As shown in FIGS. 1 to 3, the first engaged portion 21 is a rectangular region positioned at least at a position facing a central portion of the hook tape 7 in the longitudinal direction thereof (i.e., in the width direction WD), in a state in which the absorbent article for pet 1 is wrapped around the pet's waist. The first engaged portion 21 is configured of the top sheet 2.

The dimension W1 of the first engaged portion 21 in the width direction WD of the absorbent article for pet 1 is preferably 65 to 95% of the dimension W2 of the hook tape 7 in the longitudinal direction of the hook tape 7, to ensure a reliable engaged state between the first end portion 11 and the second end portion 12 upon putting the absorbent article for pet 1 on the pet.

The second engaged portion 22 is a rectangular region provided in the vicinity of the second end portion 12 at a position facing at least one of opposite ends of the hook tape 7 in the longitudinal direction of the hook tape 7, in a state in which the absorbent article for pet 1 is wrapped around the pet's waist. The second engaged portion 22 is configured of the first side sheet 51 and/or the second side sheet 52. In the first embodiment, the second engaged portion 22 is formed only on the front side portion side in the vicinity of the second end portion 12, as shown in FIG. 3, and configured of the second side sheet 52.

The second engaged portion 22 is configured to be engageable with the hook tape 7 with an engagement force that is smaller than the engagement force of the first engaged portion 21 with the hook tape 7. In the first embodiment, in order to differentiate the engagement force with the hook tape 7 between the first engaged portion 21 and the second engaged portion 22, the type and/or density of nonwoven fabric constituting the top sheet 2 and the second side sheet 52 as the first engaged portion 21 and the second engaged portion 22 are differentiated from each other.

As described above, the density of the top sheet 2 is 0.01 g/cm$^3$ to 1.0 g/cm$^3$, and the density of the second side sheet 52 is 0.001 g/cm$^3$ to 0.3 g/cm$^3$. Thus, the density of the second side sheet 52 is configured to be less than that of the top sheet 2. Here, the density of each of the top sheet 2, the back surface sheet 31 and the waterproof sheet 32, the first side sheet 51 and the second side sheet 52 is obtained as follows. First, each nonwoven fabric is cut into a 10×10 cm sample. The weight and thickness of the sample under no load is measured at an ambient temperature of 20 degrees centigrade and relative humidity of 65%. The values of the weight and the thickness are obtained respectively by averaging values obtained from the measurement of weight and thickness of ten samples.

The engagement force is obtained by the following method.

First, the hook tape is cut into a test piece of 25 mm×60 mm. An end portion of the test piece is held by a chuck by 10 mm. The nonwovenfacric such as the second side sheet 52 or the top sheet 2, which is an engagement target of the hook tape, is stuck to a stainless panel with a double-stick tape. The test piece is placed on the engagement target and engaged therewith by a pressurizing roller of 700 g moving back and forth thereon at 300 mm/min. The stainless panel is set to a measuring instrument "Autograph" manufactured by Shimadzu Corporation. An end portion of the test piece is peeled from the stainless panel such that the test piece makes 135 degrees with respect to the stainless panel. Here, a value upon disengagement is measured as the engagement force (N) and engagement strength is obtained by dividing N by a width of the test piece (25 mm in the present measurement) (N/25 mm). Peeling of the test piece is performed under conditions of: a distance in a perpendicular direction between the chuck and the test piece (hook tape) of 10 mm; a pulling rate of 300 mm/min; an ambient temperature of 20 degrees centigrade; and relative humidity of 65%.

The engagement force in the present embodiment is a value obtained by multiplying the engagement strength of the test piece thus obtained by a width of the side sheet 52 or top sheet 2, according to the embodiment.

The dimension W3 of the second engaged portion 22 in the width direction WD of the absorbent article for pet 1 is preferably 5 to 35% of the dimension W2 of the hook tape 7, for facilitating removal of the absorbent article for pet 1 from the pet's waist.

In the above-described absorbent article for pet 1, the first elastic member 61 in the extended state is fixed to the first side sheet 51 and the second side sheet 52 along the longitudinal direction LD of the absorbent article for pet 1. In addition, the second elastic member 62 in the extended state is fixed between the side sheets 51, 52 and the back surface sheet 31, along the longitudinal direction LD of the absorbent article for pet 1.

Given this, the absorbent article for pet 1 in a natural state (without external force applied) has a three-dimensional shape as shown in FIG. 1, with the first elastic member 61 and the second elastic member 62 being contracted to thereby bring the first end portion 11 and the second end portion 12 close to each other, with the top sheet side defining an inner surface. A pair of waist gather portions 13 that are stretchable in the longitudinal direction LD are thus formed in the back side portion 17 and the front side portion 18 (see FIG. 1).

In addition, the free ends of the first side sheet 51 and the second side sheet 52, mainly a portion, in which the first elastic member 61 is arranged, lifts. As a result, the first side sheet 51 forms the first raised gather portion 14 and the second side sheet 52 forms the second raised gather portion 15 (see FIG. 5).

Here, the inner edge of the first side sheet 51 constituting the first raised gather portion 14 is not joined with the top sheet 2 in an overall length in the longitudinal direction LD of the absorbent article for pet 1. In addition, the inner edge of the first side sheet 51 is folded outward in the width direction WD of the absorbent article for pet 1, and joined with the top sheet 2 in the first end portion 11 and the second end portion 12, as shown in FIGS. 4 and 6. As a result, the first raised gather portion 14 (the first side sheet 51) is configured to be easy to incline outwardly in the width direction WD of the absorbent article for pet 1, from a state in which the free end thereof is upright (see FIG. 5).

On the other hand, the inner edge of the second side sheet 52 constituting the second raised gather portion 15 is joined with the top sheet 2 in the first end portion 11 and the second end portion 12, whereas a remainder of the inner edge of the second side sheet 52 outside the first end portion 11 and the second end portion 12 is configured to be a free end. As a result, the second raised gather portion 15 (the second side sheet 52) is configured to be easy to incline inwardly in the width direction WD of the absorbent article for pet 1, from a state in which the free end thereof is upright.

Figure 8:
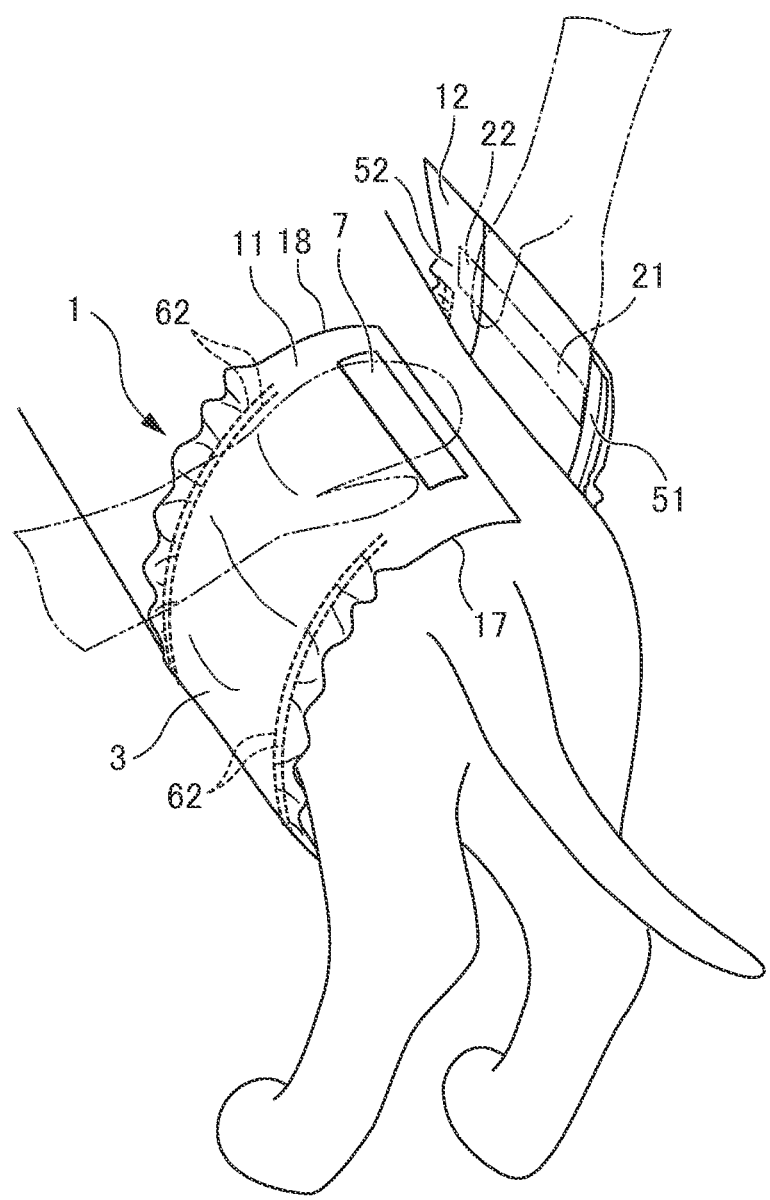
FIG. 8 is a diagram illustrating a process of putting the absorbent article for pet on a pet, in which the first end portion is placed on the pet's back.
Figure 9:
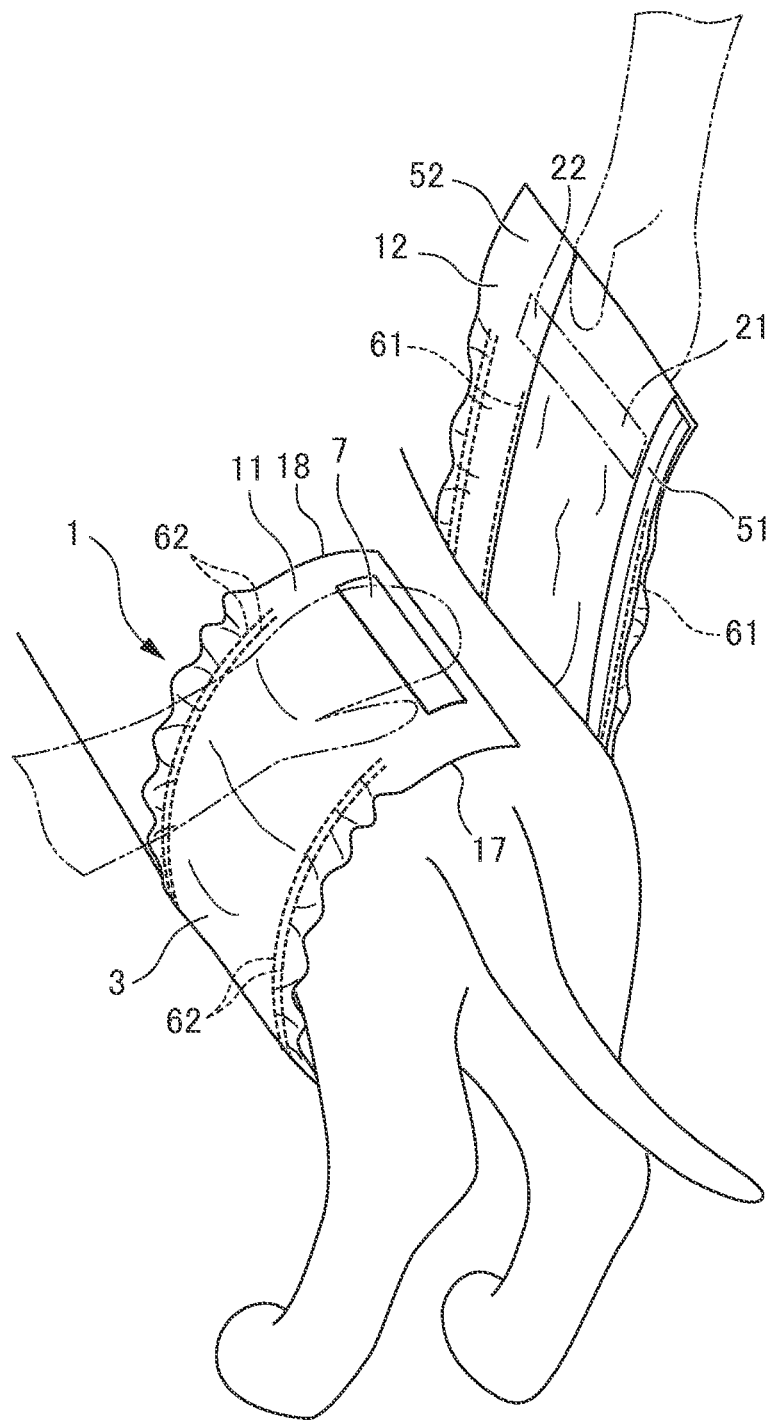
FIG. 9 is a diagram illustrating a process of putting the absorbent article for pet on a pet, in which the second end portion of the absorbent article for pet wrapped around the waist of the pet is pulled to bring the absorbent article for pet into close contact with the pet's waist.
Figure 10:
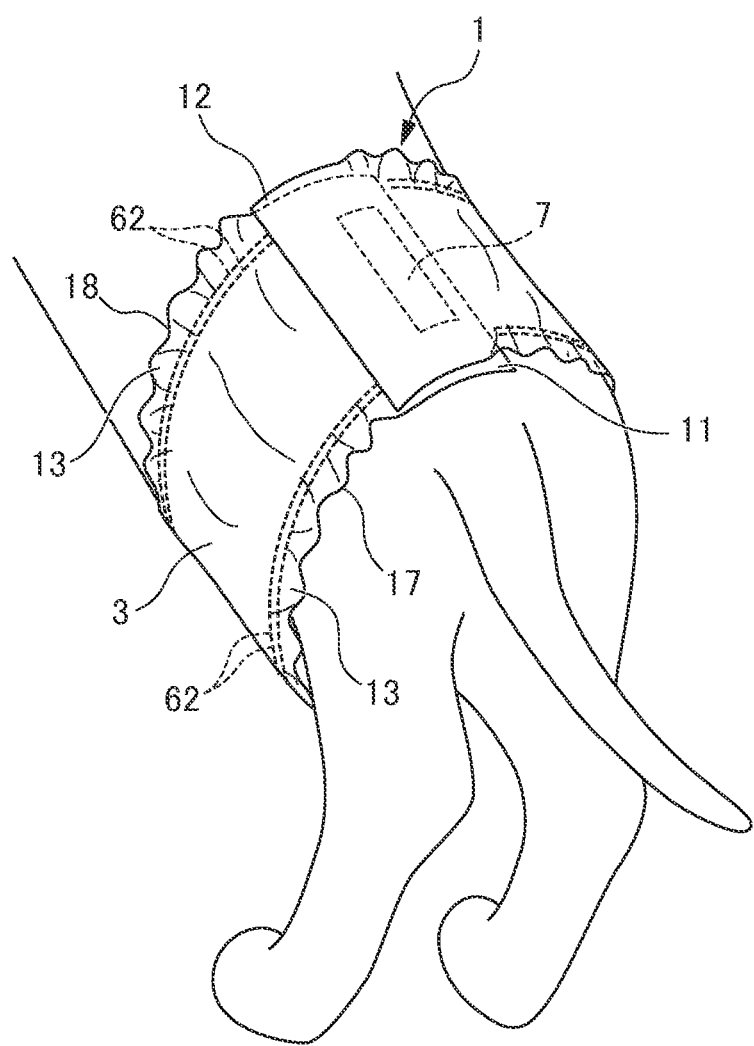
FIG. 10 is a diagram illustrating a state in which the absorbent article for pet is put around the pet's waist.

Next, steps of putting the absorbent article for pet 1 according to the first embodiment on a pet will be described hereinafter with reference to FIGS. 8 to 10. FIGS. 8 to 10 are diagrams illustrating a process of putting the absorbent article for pet 1 on a pet: FIG. 8 is a diagram illustrating a state in which the first end portion 11 is placed on the pet's back; FIG. 9 is a diagram illustrating a process of putting the absorbent article for pet on a pet, in which the second end portion of the absorbent article for pet wrapped around the waist of the pet is pulled to bring the absorbent article for pet into close contact with the waist of the pet; and FIG. 10 is a diagram illustrating a state in which the absorbent article for pet is put around the pet's waist.

First, as shown in FIG. 8, the first end portion 11 of the absorbent article for pet 1 is placed on the back of the pet and the vicinity of the first end portion 11 is held by one hand of a user. Next, in a state in which the vicinity of the first end portion 11 is held by one hand, the second end portion 12 of the absorbent article for pet 1 is held by the other hand and wrapped around the pet's body to cover the abdomen of the pet.

Next, as shown in FIG. 9, the second end portion 12 is pulled upward and the pair of waist gather portions 13 is brought into close contact with the pet's waist; and then, as shown in FIG. 10 and FIGS. 1 to 3, the first engaged portion 21 and the second engaged portion 22 arranged on the inner face of the second end portion 12 are engaged with the hook tape 7 provided on the outer face of the first end portion 11. The absorbent article for pet 1 is thus wrapped around the pet's waist in a state in which the first raised gather portion 14 inclines outward, i.e., toward the back side of the pet's body during use of the absorbent article for pet 1.

Figure 11:
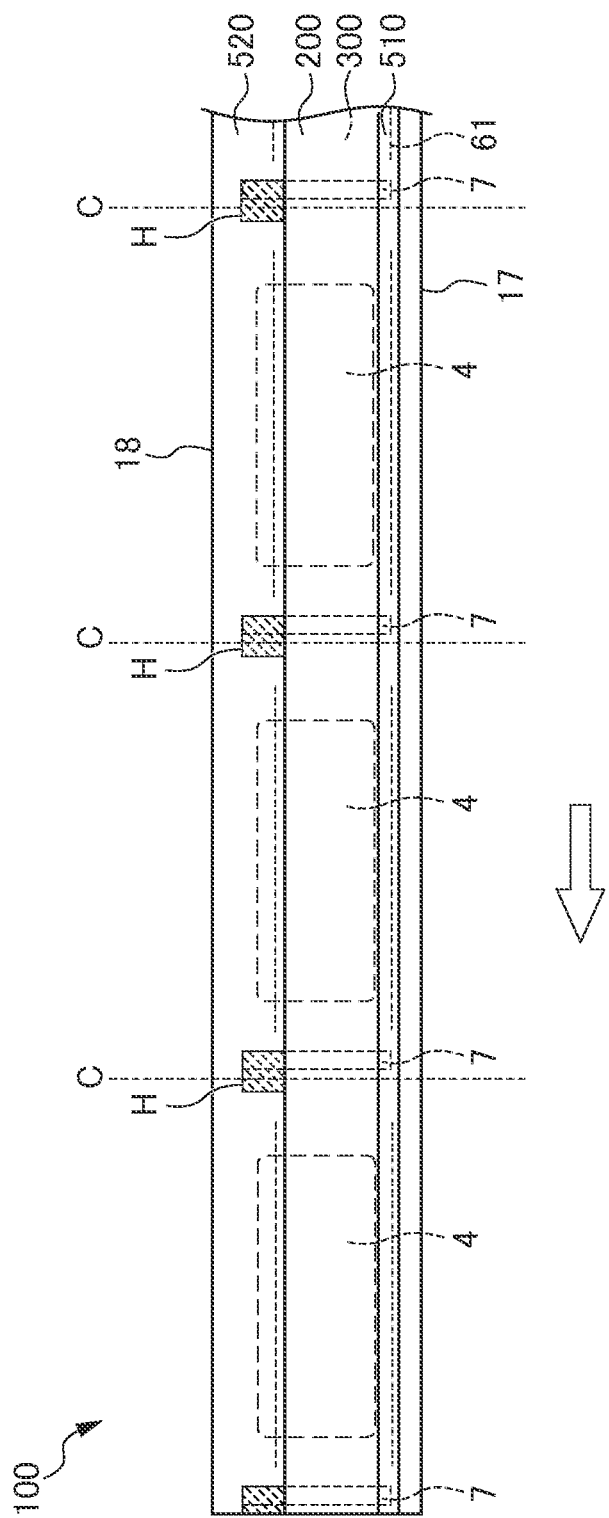
FIG. 11 is a plan view illustrating a continuous body formed in a manufacturing method of the absorbent article for pet according to the first embodiment.
Figure 12:
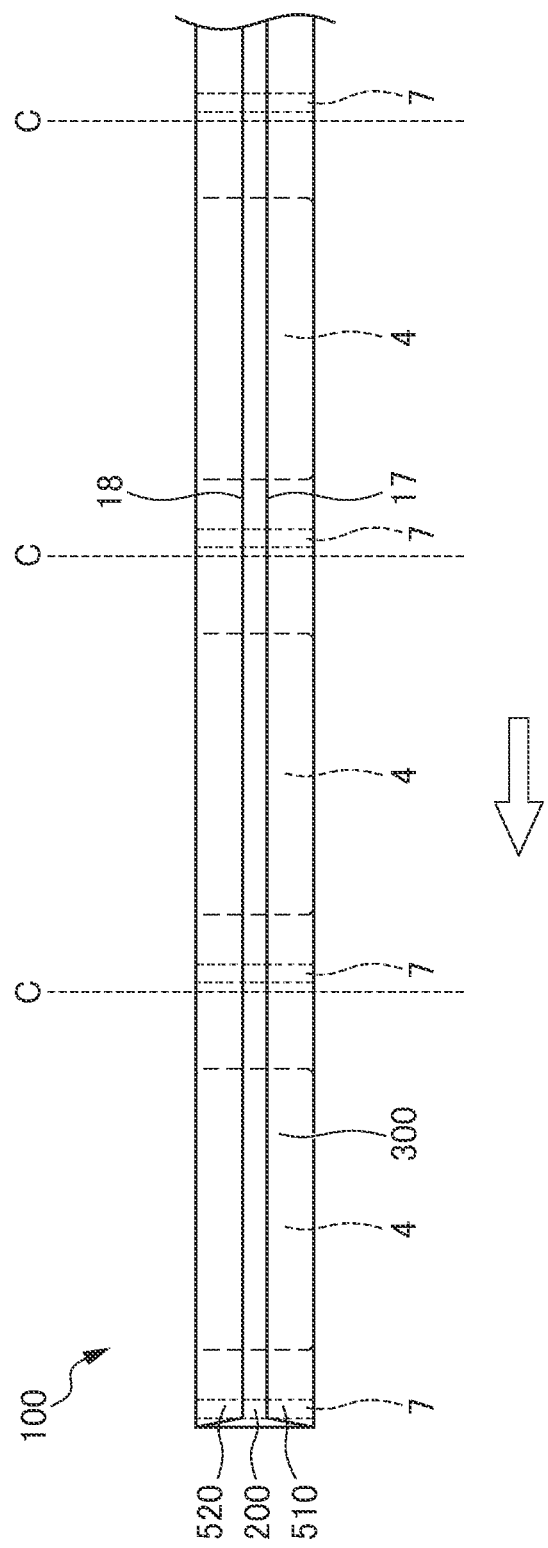
FIG. 12 is a plan view illustrating a fold-back structure in the manufacturing method of the absorbent article for pet according to the first embodiment.

Next, the manufacturing method of the absorbent article for pet 1 according to the first embodiment is described hereinafter with reference to FIGS. 11 and 12. FIGS. 11 and 12 are plan views of steps of the manufacturing method of the absorbent article for pet 1.

First, a continuous body 100 of the absorbent article for pet 1 is formed. More specifically, a plurality of absorbent cores 4 is arranged between a continuous top sheet 200 and a continuous back surface layer 300 at predetermined intervals in a longitudinal direction.

On the continuous back surface layer 300, hook tapes 7 are attached at positions where the absorbent cores 4 are not arranged.

Next, a continuous first side sheet 510 and a continuous second side sheet 520 are arranged on a pair of side portions of the continuous top sheet 200. On inner portions of the continuous first side sheet 510 and the continuous second side sheet 520, the first elastic members 61 are arranged in advance in an extended state. The inner portions of the continuous first side sheet 510 and the continuous second side sheet 520 are folded back inwards and fixed by bonding with an adhesive.

The inner side edge of the continuous first side sheet 510 is folded to outward of the continuous body 100 of the absorbent article for pet 1.

The inner side edge of the continuous second side sheet 520 and the continuous top sheet 200 are joined with the hot melt adhesive H at vicinity of cut portions C which will be cut to produce each of individual pet absorbent article for pet 1 from the continuous body 100.

In the first embodiment, as described, the first engaged portion 21 is formed with a portion of the top sheet 2 at a side of the second end portion 12. The second engaged portion 22 is formed with side sheets 52. Therefore, it is unnecessary to provide another member to form the first engaged portion 21 and the second engaged portion 22.

As shown in FIGS. 4 and 11, outer side of the continuous first side sheet 510 and the outer side of the continuous second side sheet 520 are joined with an outer side of the continuous back surface layer 300 and an outer side of the continuous top sheet 200. Here, as shown in FIG. 5, at the outer sides of the continuous top sheet 200, the second elastic member 62 is arranged and bonded between the outer side of the continuous first side sheet 510 and the continuous back surface layer 300, and also between the outer side of the continuous second side sheet 520 and the continuous back surface layer 300.

Next, as shown in FIG. 12, two side portions of the continuous body of the absorbent article for pet 100 is folded back toward the continuous top sheet 200 such that continuous first side sheet 510 and the continuous second side sheet 520 are folded back on itself in the width direction. More specifically, sides 17 of the continuous body of the absorbent article for pet 100 are folded back toward the continuous top sheet 200.

The continuous body of the absorbent article for pet 100 is cut in the width direction at predetermined intervals in the longitudinal direction.

The absorbent article for pet thus cut and shaped is double-folded such that the top sheet 2 faces itself. And then, a plurality of absorbent articles for pet 1 thus double-folded is put in a package bag in a state of being stacked (not illustrated).

The above-described absorbent article for pet 1 according to the first embodiment provides the following operation and effects.

(1) The absorbent article for pet 1 is configured to include: the first engaged portion 21 engageble with the hook tape 7 with a predetermined engagement force; and the second engaged portion 22 engageble with the hook tape 7 with an engagement force that is smaller than the engagement force of the first engaged portion 21 with the hook tape 7. The first engaged portion 21 is disposed at a position facing the central portion of the hook tape 7 in the longitudinal direction thereof (i.e., in the width direction WD), and the second engaged portion 22 is disposed at a position facing at least one of opposite ends of the hook tape 7 in the longitudinal direction thereof (i.e., in the width direction WD). As a result, upon removal of the second end portion 12 from the first end portion 11 of the absorbent article for pet 1 wrapped around the pet's waist, the second end portion 12 can be easily removed due to the smaller engagement force of the second engaged portion 22. Meanwhile, the greater engagement force of the first engaged portion 21 can prevent the second end portion 12 from dropping easily from the first end portion 11 while the absorbent article for pet 1 is wrapped around the pet's waist. Therefore, engagement between the first end portion and the second end portion is not easily released even if the pet wearing the absorbent article for pet 1 moves, while the engagement between the first end portion and the second end portion can be easily released upon removal of the absorbent article for pet 1 from the pet.

(2) The hook tape 7 is disposed on the back surface sheet 31 side (outer side) of the first end portion 11, and is engageable with the top sheet side (inner side) in the vicinity of the second end portion 12. As a result, the first engaged portion 21 can be constituted of the top sheet 2 and the second engaged portion 22 can be constituted of the second side sheet 52, and the density and/or type of the nonwoven fabric constituting the top sheet 2 can be different from the density and/or type of the nonwoven fabric constituting the second side sheet 52. Therefore, the absorbent article for pet 1 can be configured with the first engaged portion 21 and the second engaged portion 22 without employing additional components.

(3) The inner edge of the first side sheet 51 is a free end and foldable outward in the width direction WD of the absorbent article for pet 1 at the first end portion 11 and the second end portion 12. In addition, the inner edge of the second side sheet 52 is joined with the top sheet 2 in the first end portion 11 and the second end portion 12. As a result, the absorbent article for pet 1 is put on to the pet's body in a state in which the first side sheet 51 inclines outward, and the second engaged portion 22 is formed only on the side of the second side sheet 52. In other words, only the first engaged portion 21 is provided on the side of the first side sheet 51, and the second engaged portion 22 is not provided on that side. Here, the first side sheet 51, which is on the back side portion 17, is on a back side of the pet's body near the the legs that is moved more often. This allows a configuration in which the engagement force between the first end portion 11 and the second end portion 12 on the side of the first side sheet 51 is greater than on the side of the second side sheet 52, which is on the front side portion 18 that is moved less often. As a result, the absorbent article for pet 1 can be configured to be easy to peel and not easy to drop.

Figure 13:
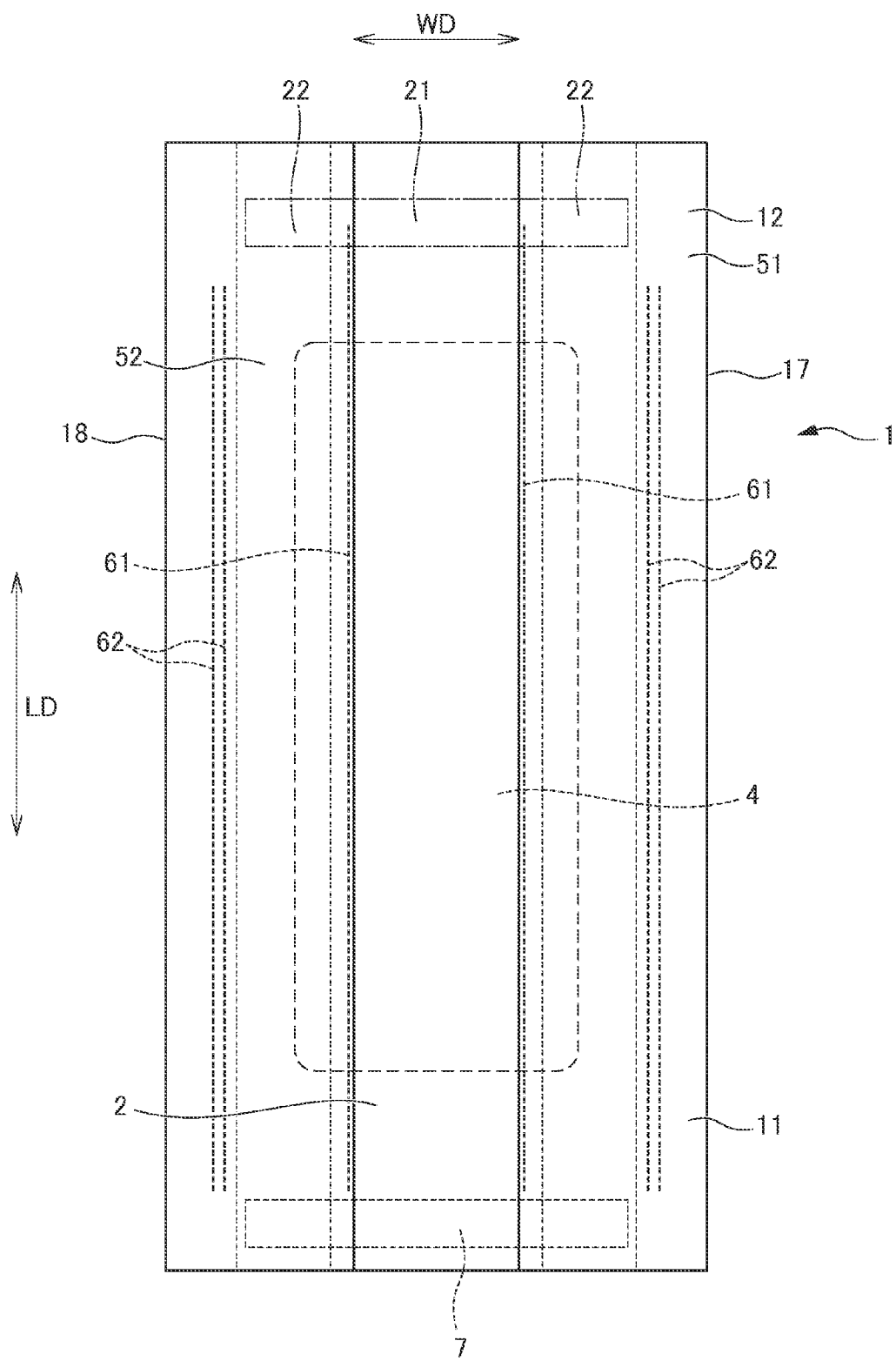
FIG. 13 is a plan view of the absorbent article for pet according to a second embodiment, as viewed from the top sheet side.

The absorbent article for pet 1 according to the second embodiment will be described hereinafter with reference to FIG. 13. FIG. 13 is a plan view of the absorbent article for pet 1 according to the second embodiment, as viewed from the top sheet side.

In the description of the following embodiments, the same constituent features as those described with respect to the first embodiment are referred by the same reference numerals and a description thereof is omitted or simplified.

The absorbent article for pet 1 according to the second embodiment is different from the first embodiment mainly in the arrangement of the second engaged portion 22.

In the second embodiment, as shown in FIG. 13, the second engaged portion 22 is provided on each side of the first engaged portion 21 in the width direction WD of the absorbent article for pet 1. In other words, a pair of second engaged portions 22 are disposed to respectively face the opposite ends of the hook tape 7. The pair of second engaged portions 22 is configured of the first side sheet 51 and the second side sheet 52, respectively.

The top sheet 2 is constituted of a hydrophilic nonwoven fabric and the first side sheet 51 and the second side sheet 52 are constituted of a hydrophobic nonwoven fabric. In addition, in the second embodiment, in order to differentiate the engagement force with the hook tape 7 between the first side sheet 51 and the second side sheet 52, the type and/or density of nonwoven fabric constituting the first side sheet 51 and the second side sheet 52 are differentiated therebetween. In other words, the second engaged portion 22 has different engagement forces with the hook tape 7, depending on whether the first side sheet 51 or the second side sheet 52 constitutes the second engaged portion 22.

In the second embodiment, the second engaged portion 22 on the side of the second side sheet 52, which is on the front side portion 18, i.e., on a front side of the pet's body, is configured to be engageable with the hook tape 7 with the engagement force that is smaller than the engagement force of the second engaged portion 22 on the side of the first side sheet 51, which is on the back side portion 17, i.e., on a back side of the pet's body, with the hook tape 7. That is, as the first side sheet 51, the nonwoven fabric having smaller density than that of the second side sheet 52 is employed.

In a case in which the second engaged portion 22 is provided on each side of the first engaged portion 21, as in the second embodiment, the dimension W1 of the first engaged portion 21 in the width direction WD of the absorbent article for pet 1 is preferably 30 to 90% of the dimension W2 of the hook tape 7 in the longitudinal direction thereof.

The absorbent article for pet 1 according to the second embodiment provides the following effects, in addition to the above effects (1) to (2).

(4) The second engaged portion 22 is arranged on both sides of the first engaged portion 21. As a result, upon removal of the second end portion 12 from the first end portion 11 of the absorbent article for pet 1 wrapped around the pet's waist, the second end portion 12 can be easily removed from both the back side portion 17 and the front side portion 18.

(5) The type of nonwoven fabric of the first side sheet 51 is differentiated from the type of nonwoven fabric constituting the second side sheet 52. As a result, the engagement force of the second engaged portion 22, which is configured of the first side sheet 51, with the hook tape 7 can be differentiated from the engagement force of the second engaged portion 22, which is configured of the second side sheet 52, with the hook tape 7. Therefore, even in a case in which two second engaged portions 22 are provided, the engagement force of the second engaged portions 22 with the hook tape 7 can be adjusted appropriately, according to potential movement of various parts of the pet, for example, the back side portion 17 that is moved more often and the front side portion 18 that is moved less often.

Figure 14:
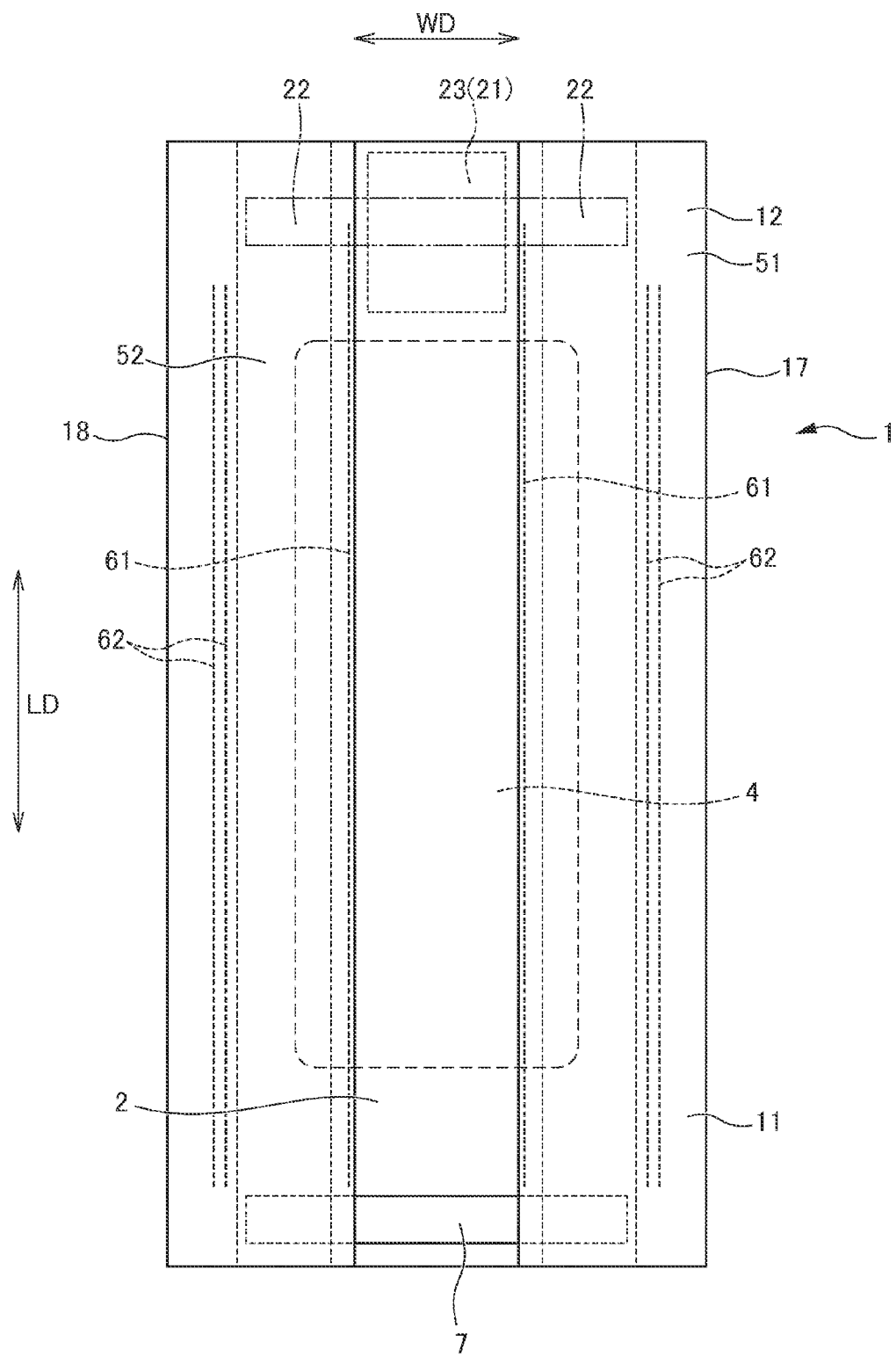
FIG. 14 is a plan view of the absorbent article for pet according to a third embodiment, as viewed from the top sheet side.
Figure 15:
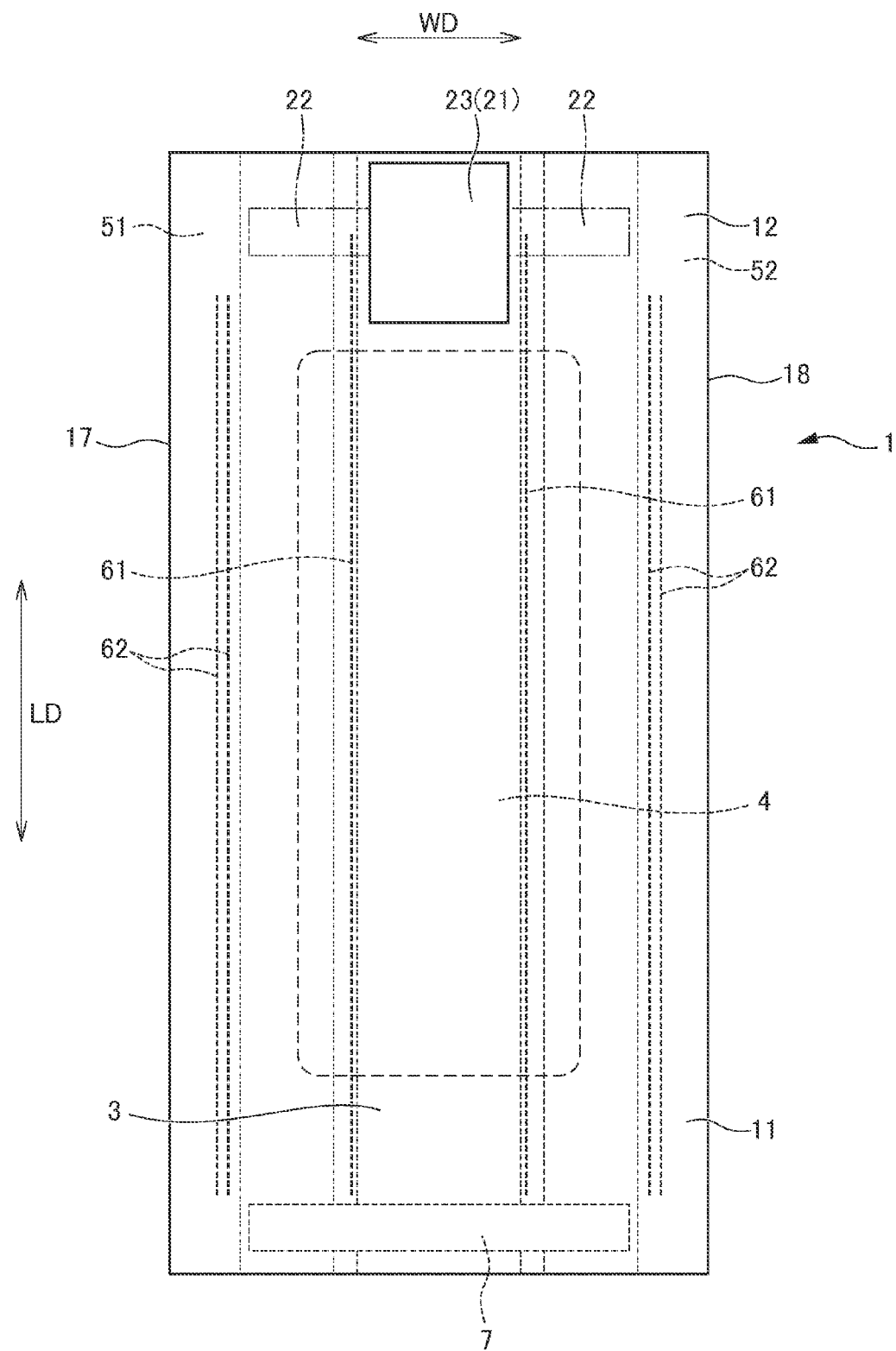
FIG. 15 is a plan view of the absorbent article for pet according to the third embodiment, as viewed from the back surface layer side.

The absorbent article for pet 1 according to the third embodiment will be described hereinafter with reference to FIGS. 14 and 15. FIG. 14 is a plan view of the absorbent article for pet 1 according to the third embodiment, as viewed from the top sheet side. FIG. 15 is a plan view of the absorbent article for pet 1 according to the third embodiment, as viewed from the back surface layer side.

The absorbent article for pet 1 according to the third embodiment is different from the first and second embodiments mainly in the arrangement of the hook tape 7, the first engaged portion 21, and the second engaged portion 22.

In the third embodiment, as shown in FIGS. 14 and 15, the hook tape 7 is disposed on the top sheet side in the vicinity of the first end portion 11. In addition, the first engaged portion 21 and the second engaged portion 22 are disposed on the back surface layer side in the vicinity of the second end portion 12.

In the third embodiment, the back surface sheet 31 is configured of a nonwoven fabric engageable with the hook tape 7.

In the third embodiment, the loop tape 23 as a loop member engageable with the hook tape 7 is disposed on the back surface sheet side in the vicinity of the second end portion 12. The loop tape 23 constitutes the first engaged portion 21. More specifically, the loop tape 23 is disposed in a substantially central portion of the absorbent article for pet 1 in the width direction WD and in the vicinity of the second end portion 12, as shown in FIG. 14. In addition, a dimension of the loop tape 23 in the width direction WD of the absorbent article for pet 1 is configured to be smaller than the dimension of the hook tape 7 in the longitudinal direction thereof. The dimension of the loop tape 23 in the longitudinal direction LD of the absorbent article for pet 1 is configured to be greater than a dimension of the hook tape 7 in the width direction thereof (i.e., in the longitudinal direction LD of the absorbent article for pet 1).

The loop tape 23 has a belt-shaped base portion and a plurality of loop portions provided on one face of the base portion. The loop tape 23 is attached to the back surface sheet 31 such that the face on which the plurality of loop portions is formed is directed outward.

In addition, in the third embodiment, the second engaged portion 22 is configured of the back surface sheet 31 positioned on both sides of the loop tape 23 in the width direction WD of the absorbent article for pet 1.

The absorbent article for pet 1 according to the third embodiment provides the following effects, in addition to the above effects (1), (2) and (4).

(6) The loop tape 23 is provided on the back surface sheet side in the vicinity of the second end portion 12, and the first engaged portion 21 is constituted of the loop tape 23. As a result, a degree of freedom of a material constituting the first engaged portion 21 can be increased, thereby allowing more stable engagement between the first end portion 11 and the second end portion 12 by constituting the loop tape 23 with a material having a greater engagement force with the hook tape 7. In addition, by using a material of a superior durability as the loop tape 23, the first engaged portion 21 can be made difficult to be damaged even if the first end portion 11 and the second engaged portion 12 are engaged repeatedly. Furthermore, since the first engaged portion 21 can be selected independently from the engagement force of the back surface sheet 31 with the hook tape 7, a degree of freedom of a material for the the first engaged portion 21 can be increased.

The preferred embodiments have been described; however, the present invention is not limited thereto and can be modified in various manners.

For example, the first side sheet 51 and the second side sheet 52 include a water-repellent or hydrophobic nonwoven fabric in the first to third embodiments; however, the present invention is not limited thereto. In other words, the first side sheet and the second side sheet can be constituted of a hydrophilic nonwoven fabric.

In addition, the absorbent article for pet 1 is configured including the first side sheet 51 and the second side sheet 52 in the first to third embodiments; however, the present invention is not limited thereto. In other words, the absorbent article for pet 1 can be configured including only any one of the first side sheet 51 and the second side sheet 52.

For example, in the first to third embodiments, the back surface layer (back sheet) 3 is constituted of two layers: the back surface sheet 31 and the waterproof sheet 32; however, the present invention is not limited thereto. In other words, the back surface layer can also be constituted only of the back surface sheet or the waterproof sheet.

In the above-described embodiments, various elements are described to have rectangular or substantially rectangular shapes; however, the present invention is not limited thereto. In other words, other shapes such as oval shape, hourglass-shape, and so on are contemplated in further embodiments.

In addition, the engaging member is described as a hook tape; however, the present invention is not limited thereto. In other words, other types of releasable fasteners are contemplated in further embodiments.

This application claims the benefit of Japanese Application No. 2011-124672 the entire disclosure of which is incorporated by reference herein.

The invention claimed is:
1. An absorbent article for pet comprising:
a liquid permeable top sheet;
a liquid impermeable back surface layer;
an absorbent core disposed between the top sheet and the back surface layer;

a first end portion and a second end portion opposing to each other in a longitudinal direction of the absorbent article;

a first side portion and a second side portion opposing to each other in a width direction of the absorbent article;

a belt-shaped engaging member disposed in the vicinity of the first end portion along the width direction of the absorbent article, the engaging member having opposite ends and a central portion between the opposite ends in a longitudinal direction of the engaging member;

a first side sheet disposed on a top sheet side of the first side portion;

a second side sheet disposed on the top sheet side of the second side portion;

a first engaged portion that is engageable with the engaging member, is disposed in the vicinity of the second end portion, and is configured to face the central portion of the engaging member in a state in which the absorbent article is wrapped around a waist of a pet; and a second engaged portion that is engageable with the engaging member with an engagement force smaller than an engagement force of the first engaged portion with the engaging member, and is configured to face one of the opposite ends of the engaging member in the state in which the absorbent article is wrapped around the waist of the pet, wherein the first engaged portion is a portion of the top sheet, the second engaged portion is a portion of at least one of the first side sheet and the second side sheet, and a dimension of the first engaged portion in the width direction of the absorbent article is 65 to 95% of a dimension of the engaging member in the longitudinal direction of the engaging member.

2. The absorbent article for pet according to claim 1, wherein the second engaged portion is configured to face only one of the opposite ends of the engaging member in the state in which the absorbent article is wrapped around the waist of the pet.

3. The absorbent article for pet according to claim 2, wherein the second engaged portion is configured to face the end of the engaging member that is to be on a front side of a body of the pet, in the state in which the absorbent article is wrapped around the waist of the pet.

4. The absorbent article for pet according to claim 1, wherein the second engaged portion includes a pair of second engaged portions configured to respectively face the opposite ends of the engaging member in the state in which the absorbent article is wrapped around the waist of the pet.

5. The absorbent article for pet according to claim 4, wherein the pair of second engaged portions have different engagement forces with the engaging member.

6. The absorbent article for pet according to claim 5, wherein the second engaged portion configured to be on a front side of a body of the pet in the state in which the absorbent article is wrapped around the waist of the pet has the engagement force with the engaging member smaller than the second engaged portion configured to be on a back side of the body of the pet in said state.

7. The absorbent article for pet according to claim 1, wherein the first side sheet has an outer edge joined with the top sheet or the back surface layer, and an inner edge at least a part of which is a free end; and the second side sheet has an outer edge joined with the top sheet or the back surface layer, and an inner edge at least a part of which is a free end.

8. The absorbent article for pet according to claim 1, wherein the first and second side sheets include non-woven fabrics; and at least one of a type and a density of the non-woven fabric constituting the first side sheet is different from the non-woven fabric constituting the second side sheet.

9. The absorbent article for pet according to claim 1, wherein the top sheet and at least one of the first and second side sheets include non-woven fabrics; and at least one of a type and a density of the non-woven fabric constituting the top sheet is different from the non-woven fabric constituting the at least one of the first and second side sheets.

10. The absorbent article for pet according to claim 7, wherein the inner edge of the first side sheet is a free end extending in an overall length of the absorbent article in the longitudinal direction of the absorbent article, the inner edge of the first side sheet in the first end portion and the second end portion is folded outward in the width direction of the absorbent article, the inner edge of the second side sheet is joined with the top sheet in the first end portion and the second end portion and free of direct attachment to the top sheet between the first and second end portions, and the second engaged portion includes a portion of the second side sheet and does not include a portion of the first side sheet.

11. The absorbent article for pet according to claim 1, wherein the engaging member includes a hook tape with a plurality of hook portions and is disposed on a back surface layer side of the vicinity of the first end portion.

12. The absorbent article for pet according to claim 1, wherein in the state in which the absorbent article is wrapped around the waist of the pet, the engaging member is configured to directly attach to (i) the liquid permeable top sheet at the first engaged portion, and (ii) at least one of the first and second side sheets at the second engaged portion.

13. The absorbent article for pet according to claim 12, wherein the first side sheet and the second side sheet are as long as the absorbent article in the longitudinal direction of the absorbent article.

14. The absorbent article for pet according to claim 1, wherein the second engaged portion includes a portion of each of the first side sheet and the second side sheet.

15. The absorbent article for pet according to claim 1, wherein the first engaged portion is a region of the top sheet at a first position configured to face the central portion of the engaging member in the state in which the absorbent article is wrapped around the waist of the pet, and the second engaged portion is a region of one of the first and second side sheets at a second position configured to face one of the opposite ends of the engaging member in the state in which the absorbent article is wrapped around the waist of the pet.

16. The absorbent article for pet according to claim 12, wherein in the state in which the absorbent article is wrapped around the waist of the pet, the engaging member is configured to be more easily removed from the second engaged portion than from the first engaged portion due to the engagement force of the second engaged portion with the engaging member being smaller than the engagement force of the first engaged portion with the engaging member.

17. An absorbent article for pet comprising:
a liquid permeable top sheet;
a liquid impermeable back surface layer;
an absorbent core disposed between the top sheet and the back surface layer;
a first end portion and a second end portion opposing to each other in a longitudinal direction of the absorbent article;
a first side portion and a second side portion opposing to each other in a width direction of the absorbent article;
a belt-shaped engaging member disposed in the vicinity of the first end portion along the width direction of the absorbent article, the engaging member having opposite ends and a central portion between the opposite ends in a longitudinal direction of the engaging member;
a first side sheet disposed on a top sheet side of the first side portion;
a second side sheet disposed on the top sheet side of the second side portion;
a first engaged portion that is engageable with the engaging member, is disposed in the vicinity of the second end portion, and is configured to face the central portion of the engaging member in a state in which the absorbent article is wrapped around a waist of a pet; and
a second engaged portion that is engageable with the engaging member with an engagement force smaller than an engagement force of the first engaged portion with the engaging member, and is configured to face one of the opposite ends of the engaging member in the state in which the absorbent article is wrapped around the waist of the pet,
wherein
the first engaged portion is constituted of a portion of the top sheet,
the second engaged portion is constituted of a portion of at least one of the first side sheet and the second side sheet, and
a dimension of the first engaged portion in the width direction of the absorbent article is 65 to 95% of a dimension of the engaging member in the longitudinal direction of the engaging member.

18. An absorbent article for pet comprising:
a liquid permeable top sheet;
a liquid impermeable back surface layer;
an absorbent core disposed between the top sheet and the back surface layer;
a first end portion and a second end portion opposing to each other in a longitudinal direction of the absorbent article;
a first side portion and a second side portion opposing to each other in a width direction of the absorbent article;
a belt-shaped engaging member disposed in the vicinity of the first end portion along the width direction of the absorbent article, the engaging member having opposite ends and a central portion between the opposite ends in a longitudinal direction of the engaging member;
a first side sheet disposed on a top sheet side of the first side portion;
a second side sheet disposed on the top sheet side of the second side portion;
a first engaged portion that is engageable with the engaging member, is disposed in the vicinity of the second end portion, and is configured to face the central portion of the engaging member in a state in which the absorbent article is wrapped around a waist of a pet; and
a second engaged portion that is engageable with the engaging member with an engagement force smaller than an engagement force of the first engaged portion with the engaging member, and is configured to face one of the opposite ends of the engaging member in the state in which the absorbent article is wrapped around the waist of the pet,
wherein
the first engaged portion includes a portion of the top sheet,
the second engaged portion includes a portion of at least one of the first side sheet and the second side sheet, and
a dimension of the first engaged portion in the width direction of the absorbent article is 65 to 95% of a dimension of the engaging member in the longitudinal direction of the engaging member.

* * * * *